(12) United States Patent
Van Der Zaag et al.

(10) Patent No.: US 10,463,349 B2
(45) Date of Patent: Nov. 5, 2019

(54) DEVICE FOR OBTAINING 3D BIOPSY (71) Applicant: KONINKLIJKE PHILIPS N.V., Eindhoven (NL)

(72) Inventors: Pieter Jan Van Der Zaag, Einhoven (NL); Cornelius Antonius Nicolaas Maria Van Der Vleuten, Eindhoven (NL); Bernardus Hendrikus Wilhelmus Hendriks, Eindhoven (NL); Gerhardus Wilhelmus Lucassen, Eindhoven (NL); Klaas Cornelis Jan Wijbrans, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 134 days.

(21) Appl. No.: 15/524,323

(22) PCT Filed: Nov. 9, 2015

(86) PCT No.: PCT/EP2015/076013
§ 371 (c)(1),
(2) Date: May 4, 2017

(87) PCT Pub. No.: WO2016/075061
PCT Pub. Date: May 19, 2016

(65) Prior Publication Data
US 2017/0319186 A1   Nov. 9, 2017

(30) Foreign Application Priority Data

Nov. 12, 2014 (EP) .................................... 14192823

(51) Int. Cl.
*A61B 10/02* (2006.01)
*A61B 5/00* (2006.01)
(Continued)

(52) U.S. Cl.
CPC ............ *A61B 10/0275* (2013.01); *A61B 1/07* (2013.01); *A61B 5/0071* (2013.01);
(Continued)

(58) Field of Classification Search
CPC ......... A61B 2010/0225; A61B 10/0233–0283; A61B 2010/0208; A61B 2010/0216
See application file for complete search history.

(56) References Cited

U.S. PATENT DOCUMENTS 5,538,008 A  *  7/1996  Crowe ................... A61B 10/06
                                                         600/564
5,573,008 A  *  11/1996 Robinson ........... A61B 10/0266
                                                         600/567
(Continued)

FOREIGN PATENT DOCUMENTS

EP  1362556 B1  3/2006
EP  2614778 A2  7/2013
(Continued)

OTHER PUBLICATIONS

Nachabe, R. et al "Estimation of Lipid and Water Concentrations in Scattering Media with Diffuse Optical Spectroscopy fro 900 to 1600 nm", Journal Biomedical Optics. vol. 15, 2010.
(Continued)

*Primary Examiner* — Devin B Henson
*Assistant Examiner* — H. Q. Nguyen (57) ABSTRACT

A biopsy device for taking a 3D biopsy may comprise an outer sleeve, a hollow main shaft, a biopsy tube and a tube shaft. The hollow main shaft may have a distal end portion with a sideward facing notch, and the main shaft may be adapted to be accommodated within the outer sleeve. The biopsy tube may be provided for receiving cut and thus isolated tissue. A proximal end of the biopsy tube may be releasably attachable to a distal end of the tube shaft so that
(Continued)

the biopsy tube is movable together with the tube shaft within the hollow main shaft between a proximal position in which the biopsy tube is not located in the notch, and a distal position in which the biopsy tube is located in the notch.

15 Claims, 7 Drawing Sheets (51) Int. Cl.
*A61B 1/07* (2006.01)
*A61B 10/04* (2006.01)
(52) U.S. Cl.
CPC .......... *A61B 5/0073* (2013.01); *A61B 5/0075* (2013.01); *A61B 5/0084* (2013.01); *A61B 5/6848* (2013.01); *A61B 10/0283* (2013.01); *A61B 2010/045* (2013.01)

(56) References Cited

U.S. PATENT DOCUMENTS

| | | | |
|---|---|---|---|
| 6,050,955 A * | 4/2000 | Bryan | A61B 10/0266 600/564 |
| 6,322,522 B1 * | 11/2001 | Zimmon | A61B 10/0096 600/565 |
| 6,656,132 B1 | 12/2003 | Ouchi | |
| 7,419,472 B2 | 9/2008 | Hibner | |
| 7,608,048 B2 | 10/2009 | Goldenberg | |
| 7,896,817 B2 | 3/2011 | Garrison | |
| 8,262,586 B2 * | 9/2012 | Anderson | A61B 10/0275 600/567 |
| 8,282,574 B2 | 10/2012 | Coonahan | |
| 8,491,496 B2 | 7/2013 | Hibner | |
| 8,679,032 B2 | 3/2014 | Mark | |
| 8,702,623 B2 | 4/2014 | Parihar | |
| 2002/0029006 A1 | 3/2002 | Turturro | |
| 2009/0124928 A1 * | 5/2009 | Zimmon | A61B 10/04 600/563 |
| 2011/0105839 A1 * | 5/2011 | Hoffman | A61B 10/06 600/104 |
| 2012/0068085 A1 | 3/2012 | Cucin | |
| 2013/0030323 A1 | 1/2013 | Smith | |

FOREIGN PATENT DOCUMENTS

| | | |
|---|---|---|
| WO | 2007021904 A2 | 2/2007 |
| WO | 2007134100 A2 | 11/2007 |
| WO | 2014068468 A1 | 5/2014 |

OTHER PUBLICATIONS

Verhaegh, W. et al, "Selection of personalized patient therapy through the use of knowledge-based computational models that identify tumor-driving signal transduction pathways" Cancer Res (2014).

Reich, C. "Specification for Photonic Biopsy Tool", 2012.

* cited by examiner

DEVICE FOR OBTAINING 3D BIOPSY

CROSS-REFERENCE TO PRIOR APPLICATIONS

This application is the U.S. National Phase application under 35 U.S.C. § 371 of International Application No. PCT/EP2015/076013, filed on Nov. 9, 2015, which claims the benefit of European Patent Application No. 14192823.4, filed on Nov. 12, 2014. These applications are hereby incorporated by reference herein.

FIELD OF THE INVENTION

The invention generally relates to a system for obtaining a 3D biopsy. Particularly, the invention relates to a biopsy device with a biopsy tube maintaining the integrity of an extracted tissue volume.

BACKGROUND OF THE INVENTION

For the proper analysis of tumours and defining the appropriate treatment detailed information on a tumour may be needed. First the presence and position of a potential tumour may be identified through medical imaging.

Figure 1:
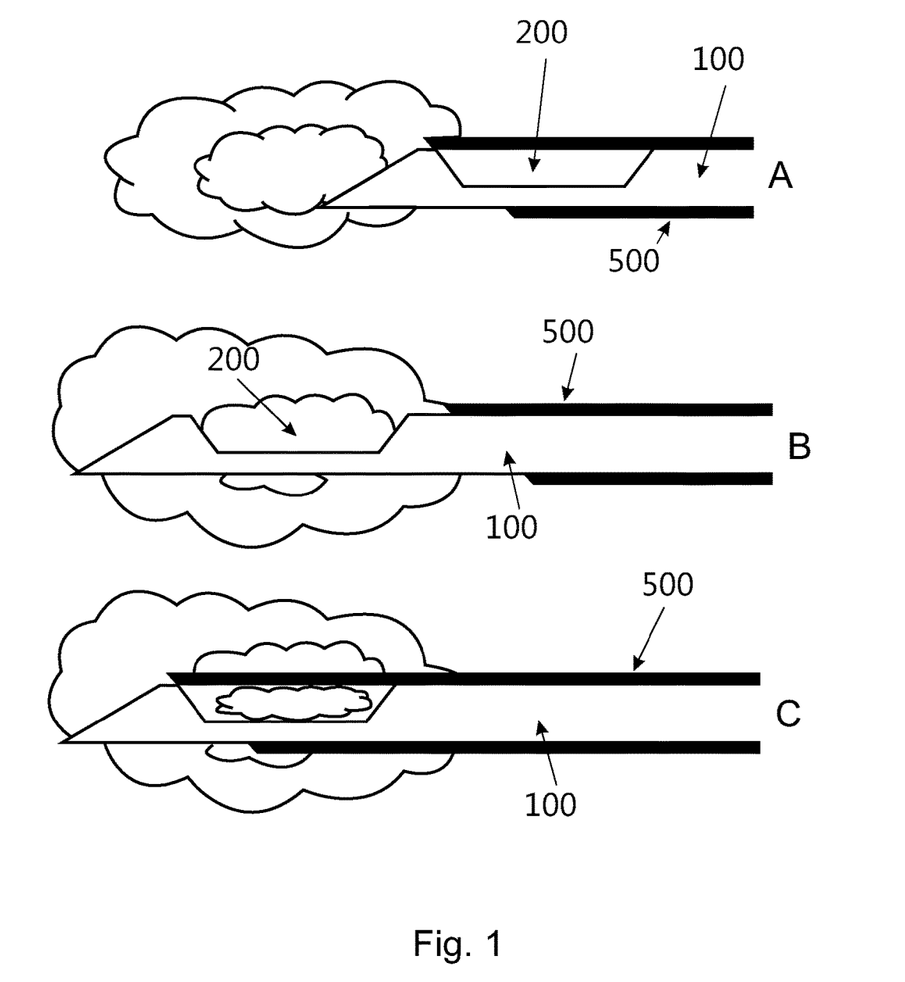
FIG. 1 illustrates steps of taking a biopsy with a known needle.

Subsequently a biopsy may be taken to assess whether or not the lesion is benign or malignant through pathology. An exemplary workflow for obtaining a biopsy is depicted in FIG. 1. For positioning the biopsy device (usually a needle with a shaft 100 having a lateral recess 200, and an outer tubular member 500) accurately in the suspicious tissue, the correct location is commonly determined using image guidance such as Ultrasound or X-ray. While imaging may provide coarse guidance of the needle towards the region of interest, it is often challenging to precisely identify the boundaries of small lesions or tumours with the biopsy needle using standard imaging modalities. As a consequence, biopsies are often taken at the wrong location, which increases the risk of false diagnoses.

Finally molecular diagnostic (MDx) analysis of the tissue may be done to determine which molecular mutations and molecular pathway drive the tumour in order to arrive at a proper treatment. In order to provide the correct molecular analysis, also tumour heterogeneity may be assessed to determine whether a single cancerous clone is responsible for the tumourous growth or whether multiple clones are present, so that possibly multiple biological pathways drive tumour growth and rather a combination of drugs should be given.

US 2012/006 8085 describes a tissue collection device having a cylindrical optically transparent tissue collection tube with two sets of spaced apart micro-pores formed along one side of the optical transparent walls thereof, a micro-occluder that slides about the outer surface of the cylindrical tissue collection tube to selectively occlude the micro-pores, a distal cap for sealing off the open distal tip portion of the tissue collection tube, and a proximal cap for sealing off the open proximal end opening of the tissue collection tube.

SUMMARY OF THE INVENTION

In view of the above mentioned problems, it can be seen as an object of the invention to get an intact 3D biopsy so that an appropriate analysis can be made.

This and further objects are solved by the subject-matter of the independent claim. Further embodiments are described in the dependent claims.

A device in accordance with the invention allows for a simpler sample handling. The biopsy stays in one piece, which is advantageous for the correlation of any pathology and MDx results to the medical imaging data/pictures. This approach enables a comparison and correlation of metabolomic markers for tumour activity (as derived from the photonic needle), molecular diagnostic markers such as obtained from molecular test such as PCR and/or sequencing from the tumour biopsy, and medical imaging data (obtained by modalities such MRI, ultrasound). In addition, the biopsy tube enables the subsequent selection of a section of the biopsy by optical imaging for further analysis by MDx or (digital) pathology.

Moreover, a tumour heterogeneity map can be made which facilitates determining the appropriate drug cocktail as well as following the tumour response via imaging.

To achieve all these advantages, a biopsy tube is generally proposed for use with a biopsy device. The biopsy tube may be made of a transparent material such as, for example, glass or a hard plastic material. According to an embodiment, the biopsy tube may be coated with a coating, which may reduce the friction such as a silicone coating, within the biopsy tube. In an example, the biopsy tube may be coated with a coating, which may reduce the friction such as a silicone coating, on the outside of the biopsy tube. In one example, the coating is provided inside the biopsy tube, and in another example, the coating is provided on the outside of the biopsy tube. In a further example, the coating is provided inside and on the outside of the biopsy tube.

According to an example, the biopsy tube may have a length between 9 mm and 19 mm, preferably 14 mm and may have an outer diameter up to 2 mm, with an inner diameter up to 1.6 mm.

Furthermore, the biopsy tube may have an inclined end with an inclination angle of about 50 to 60 degrees, so as to form a pointed tip. In such an embodiment, it may be of interest to control the rotational orientation of the biopsy tube relative to the tube shaft. To achieve this, the biopsy tube may have an alignment feature like a groove for an engagement with a corresponding protrusion at the tube shaft. Alternatively, a flat edge on an outer surface of the biopsy tube may be used to identify a rotational orientation.

According to another example, the biopsy tube may comprise a sharp edge at an end of the biopsy tube, which end will thus be configured to cut tissue when being pushed forward (distally) by means of a biopsy device. The sharp edge may preferably be provided at the pointed tip.

According to a further example, the biopsy tube may have a barcode identifier in order to permit identification of the biopsy tube and/or of the biopsy tissue located within the biopsy tube.

Generally, a biopsy device for taking a 3D biopsy may comprise an outer sleeve, a hollow main shaft, a biopsy tube and a tube shaft. The hollow main shaft may have a distal end portion with a sideward facing notch, and the main shaft may be adapted to be accommodated within the outer sleeve. It is noted that the sideward facing notch may also be an upwardly or downwardly facing notch, depending on the point of view.

The outer sleeve may be movable relative to the main shaft between a first position in which the notch is not covered by the outer sleeve, and a second position in which the notch is covered by the outer sleeve. The outer sleeve may have a sharp distal edge, wherein the sharp distal edge may be provided to cut tissue which is present in the notch so that the tissue can be isolated from surrounding tissue.

The biopsy tube is provided for receiving isolated tissue. A proximal end of the biopsy tube may be releasably attachable to a distal end of the tube shaft so that the biopsy tube is movable together with the tube shaft within the hollow main shaft between a proximal position in which the biopsy tube is not located in the notch, and a distal position in which the biopsy tube is located in the notch.

The biopsy tube may be adapted to be inserted into the notch so as to be attached to the distal end of the tube shaft, when the outer sleeve is in the first position.

Alternatively, biopsy tube may be adapted to be inserted into main shaft more proximally. The outer sleeve may comprise a side opening and the hollow main shaft may comprise a side recess, with the side recess being arranged proximally to the notch. To allow an insertion of the biopsy tube through the side opening of the outer sleeve and into the side recess of the main shaft, the outer sleeve may be movable relative to the main shaft to a third position in which the side opening is located over the side recess. By inserting the biopsy tube that way, it can be attached to the distal end of the tube shaft. It is noted that the third position may be identical with the first position in which the outer sleeve does not cover the notch.

According to an example, the outer sleeve may comprise an inwardly protruding edge at or near the distal edge of the outer sleeve for an abutment of a distal end of the biopsy tube. As long as the biopsy tube abuts to the inwardly protruding edge, the position of the biopsy tube within the main shaft and the outer sleeve can be controlled and the biopsy tube may be movable together with the tube shaft and the outer sleeve relative to the main shaft.

Further, the tube shaft may comprise a distal end with a smaller diameter so as to engage with one of the ends of the biopsy tube. Otherwise, the tube shaft may have a portion with a larger inner diameter so as to allow the biopsy tube to be inserted into that portion.

According to a further example, a suction channel may be provided in the tube shaft.

Furthermore, at least one optical fibre may be provided in the biopsy device, with a distal end of the optical fibre being arranged in the vicinity of the notch, for emitting and receiving of light, allowing in-vivo tissue inspection including at least one out of the group consisting of diffuse reflectance spectroscopy, fluorescence spectroscopy, diffuse optical tomography, differential path length spectroscopy, and Raman spectroscopy.

The tube shaft may be formed as a hollow tube shaft, the biopsy device further comprising an elongated fibre body with the at least one optical fibre being arranged within the fibre body. According to an example, the fibre body may be movably accommodated within the tube shaft, movable between a first position in which the fibre body extends through the biopsy tube so that the distal end of the optical fibre is located at the distal end of the main shaft, and a second position in which the distal end of the at least one optical fibre is located proximally to the notch.

Using a biopsy device with optical fibres, for biopsy taking, may have the following advantages:

By measuring the optical spectrum of the surrounding tissue, one may determine whether the tumour/lesion has been reached, so that one may have a better chance of successfully taking a biopsy from the tumour.

The metabolomic activity, through the NADH/FAD ratio, can be determined from the optical spectrum.

By tissue sensing at the tip, it can be ensured that the device is correctly positioned at the location of interest. A biopsy may be obtained from exactly the same location as the tissue sensing by advancing only the main shaft until the notch is at the location of interest.

A further tissue sensing of the tissue in the notch may be performed to control as to whether the correct tissue sample is captured in the notch of a biopsy device.

In the following, geometrical aspects will be defined for a better understanding. First of all, the device includes a longitudinal axis. Here, the longitudinal axis is understood as the center axis, and in particular as the center axis of a rotationally symmetrical shaft. Further, the tip portion of the device, which is the end portion of the device which will be introduced first into a body, may be cut at an angle to the main axis forming a bevel. The pointed tip of the bevel is directed to the 'front' of the needle. As a result, looking from the 'side', it is possible to recognize the angle between the bevel and the main axis, and further it is possible to look onto and into a recess formed at the side, i.e. laterally. The term 'distal' means to the front and the term 'proximal' is used to define a direction opposite to distal, i.e. to the back of a device or element.

According to another example, the biopsy device may further comprise a channel for injecting or extracting a fluid. Such a channel may be an additional channel formed in the main shaft, in the tube shaft or in a fibre body and may extend through that shaft or body in a longitudinal direction, but may also be formed between for example the fibre body and the shaft or between the shaft and the outer sleeve.

According to a further embodiment, the biopsy device may further comprise a tissue retraction channel, wherein a suction device may apply vacuum to the channel for retracting a sample of tissue. For example, the channel in which the fibre body is accommodated within the tube shaft may be used for retracting a sample, after removing the fibre body. Alternatively, the channel may be formed in the fibre body between optical fibres which are preferably arranged as much as possible at opposite sides of the elongated body.

According to an embodiment, the biopsy device may further comprise a console including a light source, a light detector and a processing unit for processing the signals provided by the light detector, wherein one of the light source and the light detector may provide wavelength selectivity. The light source may be one of a laser, a light-emitting diode or a filtered light source, and the console may further comprise one of a fibre switch, a beam splitter or a dichroic beam combiner. Furthermore, the device may be adapted to perform at least one out of the group consisting of diffuse reflectance spectroscopy, diffuse optical tomography, differential path length spectroscopy, and Raman spectroscopy.

The system may further comprise a device adapted for ex-vivo tissue inspection, and/or a storage container for receiving extracted tissue in the biopsy tube and for storing pathology information obtained by an in-vivo tissue inspection and/or an ex-vivo tissue inspection.

The aspects defined above and further aspects, features and advantages of the present invention may also be derived from the examples of embodiments to be described hereinafter and are explained with reference to examples of embodiments. The invention will be described in more detail hereinafter with reference to examples of embodiments but to which the invention is not limited.

BRIEF DESCRIPTION OF THE DRAWINGS

The illustration in the drawings is schematically only and not to scale. It is noted that similar elements are provided with the same reference signs in different figures, if appropriate.

DETAILED DESCRIPTION OF EMBODIMENTS

Figure 2:
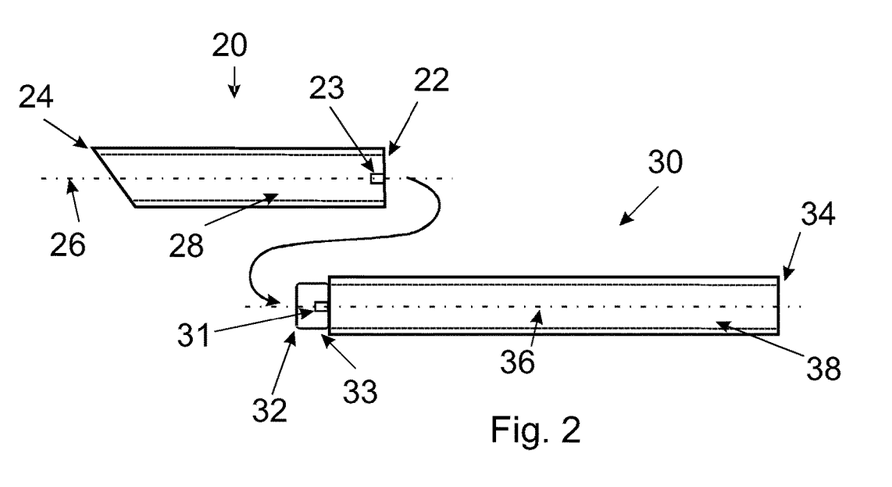
FIG. 2 shows a biopsy tube and a tube shaft.

In FIG. 2, embodiments of a biopsy tube 20 and a tube shaft 30 are shown. The biopsy tube 20 is substantially formed as a hollow cylinder with a substantially circular outer cross section and with first and second ends each having a straight edge. In this embodiment, the first end 22 is formed with an angle of 90° relative to the longitudinal axis 26, i.e. substantially perpendicular to the longitudinal axis. The second end 24 may be formed with an inclined angle relative to the longitudinal axis 26, wherein this angle may be in the range between 45° and 65°, for example 55°. It will be understood that the angles at the ends of the biopsy tube may be adapted to fit to inclined surfaces of a notch formed in a main shaft of a biopsy device, as described in detail below. For example, the length of such a biopsy tube may be between approximately 3 mm and 20 mm, preferably 14 mm +/−5 mm and an outer diameter may be 2 mm, whereas an inner diameter of a channel 28 which extends through the cylinder, may be between 1.4 and 1.6 mm. The biopsy tube may be made of glass or from a hard and transparent plastic such as PMMA. Alternative hard plastics could be Pes (polyester), PC (polycarbonate), PSU (polysulfon), PES (polyethersulfon), or Teflon. Furthermore, the biopsy tube 20 may be provided with a sharp edge at one end, in particular at the leading end, i.e. the distal end when the biopsy tube is pushed forwards by the tube shaft 30. As an alignment feature, the biopsy tube 20 is exemplarily provided with a groove 23 at the first end 22, which groove 23 may be configured for an engagement with a protrusion 31 formed at or adjacent to the first end 32 of the tube shaft 30. Such alignment features may also be useful in identifying the rotational orientation of a resected sample during later handling and analysis. In an embodiment in which a beveled leading edge is used, as shown in FIG. 2, it may further ensure that the cutting takes place with the cutting edge of the biopsy tube at the correct orientation with respect to the notch.

The tube shaft 30, as shown in FIG. 2, includes a first end 32 and a second end 34. The first end 32 as well as a short portion 33 may have a reduced diameter which is adapted to engage within one of the ends of the biopsy tube. The tube shaft 30 may also be formed as a hollow cylinder. The tube shaft may have a through bore 38 which may provide several functions. The through bore 38 may have a smaller diameter sufficient for injecting or retracting a fluid through the shaft or may have a greater diameter sufficient for allowing retraction of tissue. In a case in which the diameter of the through bore 38 in the tube shaft is equal or at least similar to the inner diameter of the biopsy tube 20, a separate element like a fibre body may be inserted and movably accommodated within the combination of the biopsy tube and the tube shaft.

Figure 3:
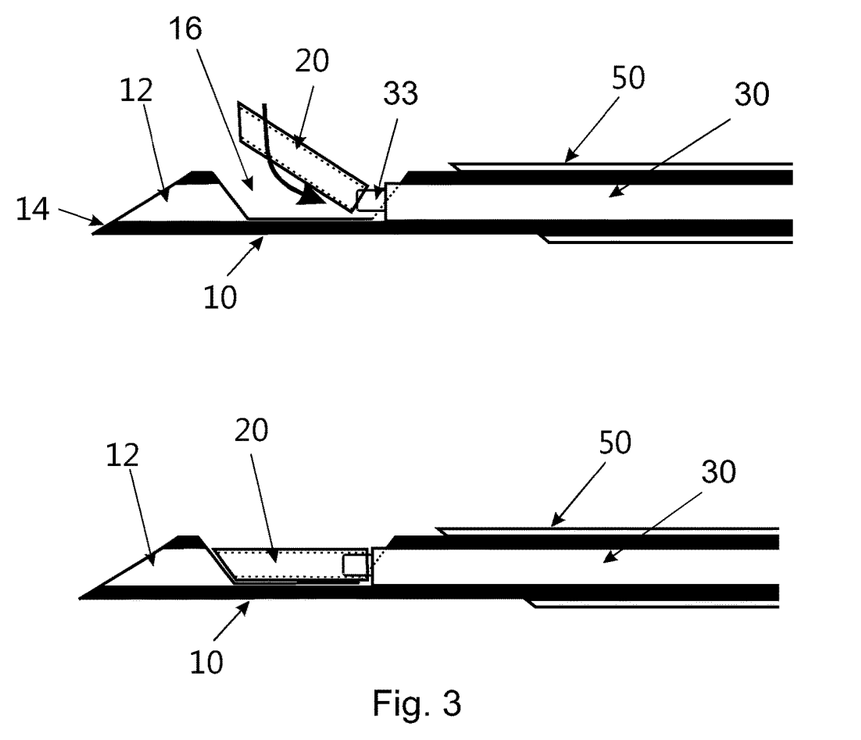
FIG. 3 illustrates steps of inserting a biopsy tube into a notch of a main shaft of a biopsy device, according to a first embodiment.

The biopsy device as shown in FIG. 3 comprises a hollow shaft 10 with a distal end or tip 14 forming a slanted surface, wherein the slanted surface may have an oval shape in case the hollow shaft has a circular cross section. Furthermore, a lateral recess or notch 16 is formed in the shaft, wherein the notch 16 is substantially formed by a lateral opening and a section of the bore extending through the shaft in a longitudinal direction. FIG. 3 further illustrates as to how a biopsy tube 20 may be inserted into a notch 16 of a main shaft 10 of a biopsy device so as to be attached at the distal end 32 of the tube shaft 30.

For example, the biopsy tube 20 may be inserted with an inclined orientation and with the proximal end 22 first. This may have the advantage that an attachment of the biopsy tube to the distal end of the tube shaft may be better controlled by hand. The kind of movement of this example is indicated by the bolt arrow in FIG. 3.

Alternatively, the biopsy tube 20 may be inserted into the notch 16 of the main shaft 10 with a parallel orientation of the longitudinal axis of the biopsy tube and the longitudinal axis of the main shaft. In this case, the tube shaft 30 may be pulled a few millimeters backwards, i.e. proximally, to provide sufficient space for the biopsy tube to be inserted into the notch. Subsequently, the tube shaft 30 may be pushed forwards, i.e. distally, so that the portion 33 with the reduced diameter may engage the biopsy tube so as to attach the biopsy tube to the tube shaft.

Figure 4:
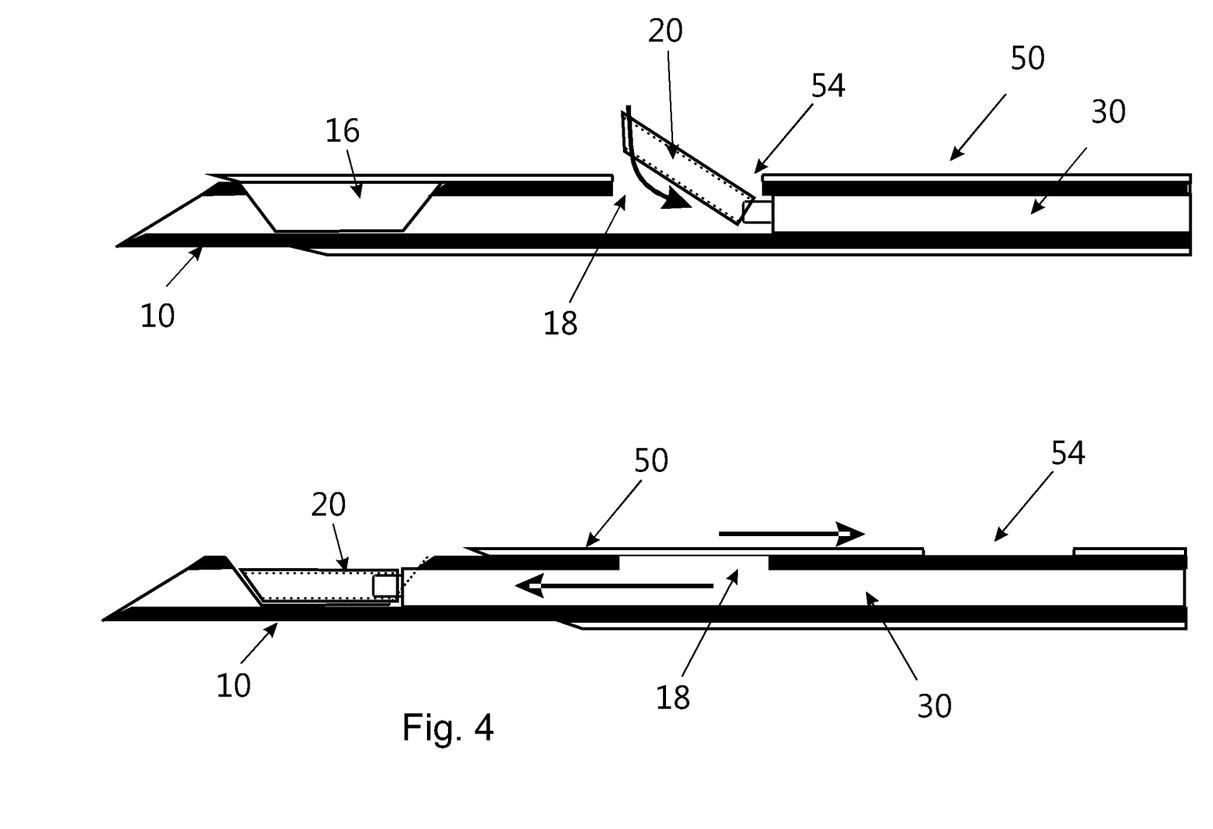
FIG. 4 illustrates steps of inserting a biopsy tube into a recess of a main shaft of a biopsy device, according to a second embodiment.

FIG. 4 shows another embodiment providing an additional recess for inserting a biopsy tube into the main shaft of the biopsy device at a location more proximal. In this embodiment, the outer sleeve 50 comprises a side opening 54 and the main shaft 10 comprises a recess 18. The outer sleeve 50 can be moved relative to the main shaft 10 so that the side opening 54 is positioned over the recess 18. As soon as the tube shaft 30 is retracted behind the opening as well as the recess, a biopsy tube 20 can be inserted in a similar way as described above. After insertion of a biopsy tube, the tube shaft 30 together with the biopsy tube 20 can be moved forwards and the outer sleeve backwards so that the recess in the main shaft is covered by the outer sleeve and the biopsy tube is located within the notch in the main shaft.

Figure 5:
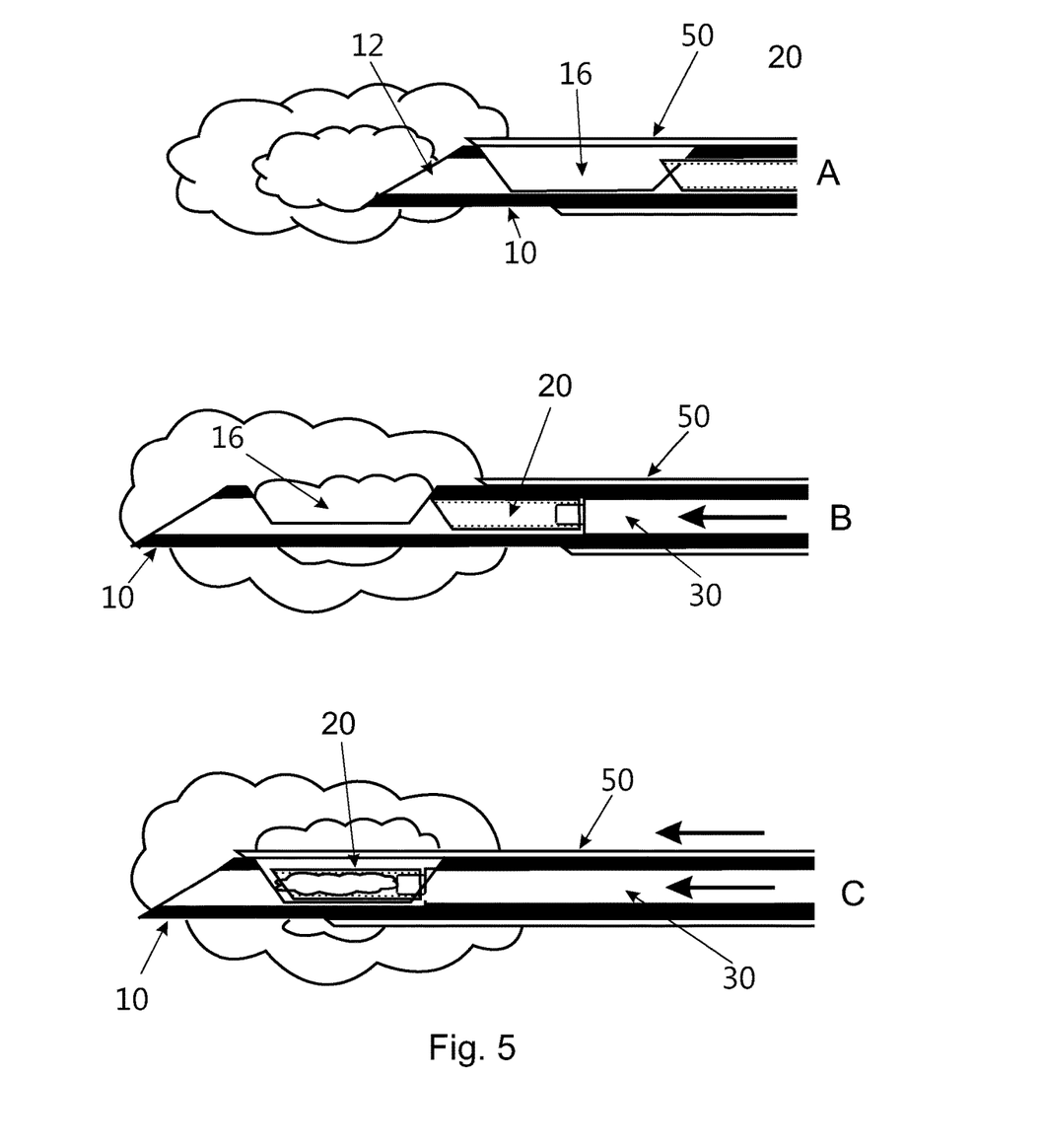
FIG. 5 illustrates steps of taking a biopsy with a biopsy device of FIG. 3 or 4.

FIG. 5 shows a sequence of steps of taking a biopsy by means of a biopsy device including, inter alia, a biopsy tube 20 for receiving tissue. Firstly, with the notch 16 of the main shaft 10 being covered by the outer sleeve 50, the biopsy device is inserted into tissue. Secondly, the main shaft is pushed forward until the notch in the main shaft is no longer covered so that tissue can engage the notch 16. Thirdly, the outer sleeve 50 which is provided with a sharp distal edge in accordance with this example, is pushed forwards so as to cut the tissue and the tube shaft 30 with the biopsy tube 20 is pushed forward so as to receive the cut tissue. It is noted that the outer sleeve 50 may also have a blunt distal edge, i.e. not a sharp distal edge, and that the biopsy tube 20 may be provided with a sharp distal edge, so that tissue which is present in the notch 16 of the main shaft 10 can be cut by means of the biopsy tube 20.

Figure 6:
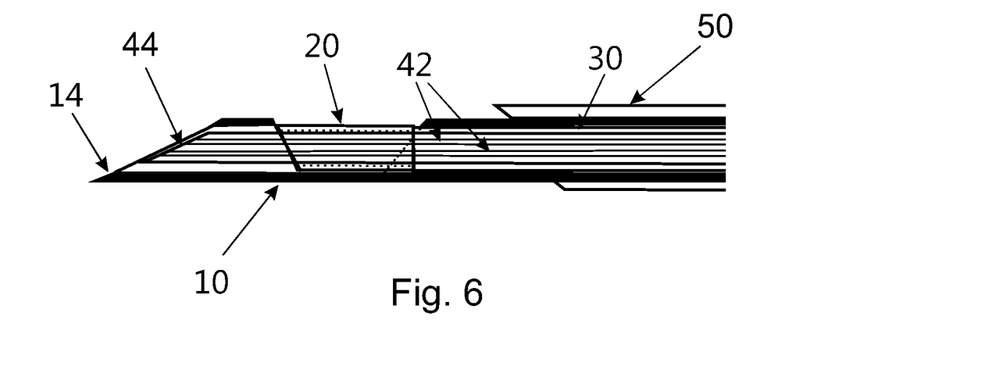
FIG. 6 shows a biopsy device including a fibre body.

FIG. 6 shows another embodiment of a biopsy device, wherein this embodiment mainly differs from the above described embodiments in that additionally a fibre body 40 is inserted through the tube shaft and the biopsy tube. The fibre body 40 may be formed by an elongated and solid element in which channels for accommodating optical fibres 42 are provided. The fibre body may include an end surface 42 forming a bevel at the distal end of the fibre body.

An optical fibre 42 may be provided for illuminating and collecting light, with a distal end of the optical fibre at the tip, i.e. at the end surface 44 of the fibre body. The proximal end of the fibre may be connected to an optical console capable of emitting and receiving light.

For optimal tissue sensing, it may be advantageous to guide at least two optical fibres 44 (source and detector) towards the tip, with the fibre tip ends having a maximized distance from each other.

Figure 7:
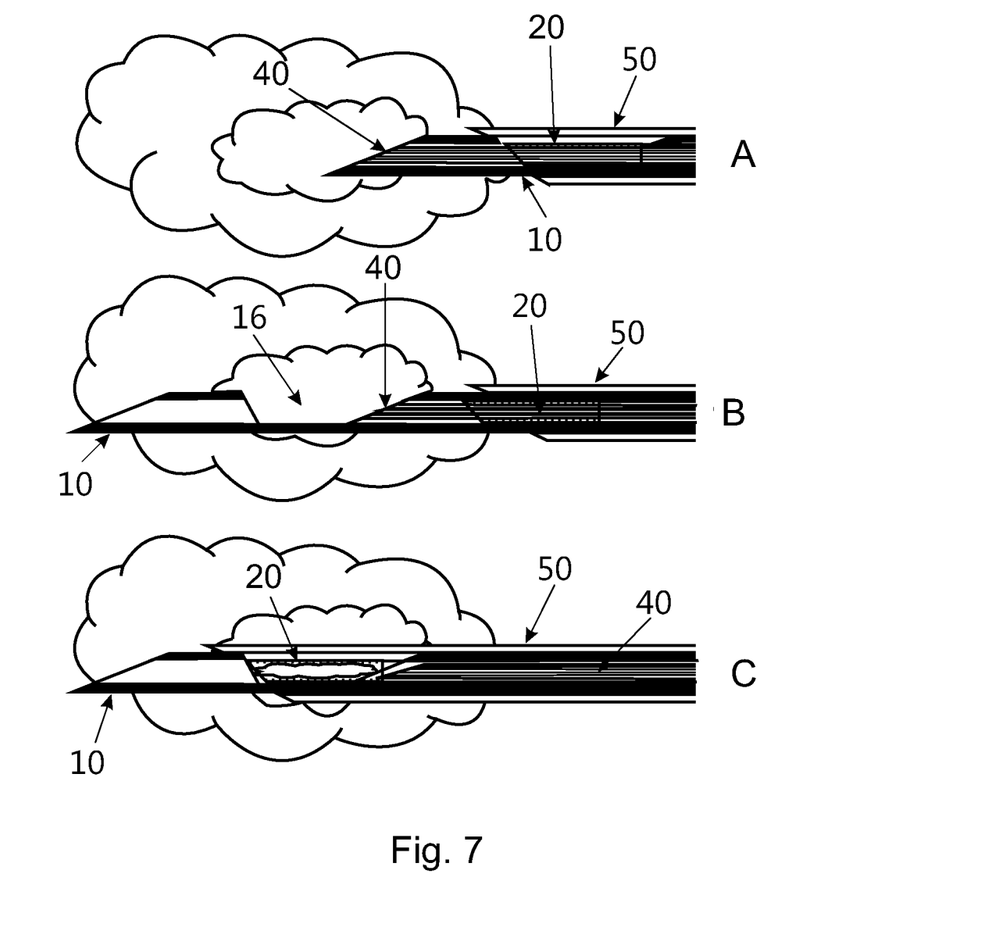
FIG. 7 illustrates steps of taking a biopsy with a biopsy device of FIG. 6.

In a typical clinical workflow as shown in FIGS. 7A to 7C, the biopsy device is inserted into the patient with the outer sleeve 50 (a cutting cannula) covering the notch 16 of the shaft 10 to ensure a smooth protrusion (step A in FIG. 7). Hence the notch 16 is not exposed to the tissue in this step, and the hollow space in the shaft 10 (including the notch 16) can be occupied by the fibre body without altering the workflow. Thus, an additional tissue characterization at the tip is possible during needle positioning.

At the target location, the shaft 10 is ejected whereas the fibre body 40 remains in its position (step B in FIG. 7). Thereby, the notch 16 is no longer occupied by the outer sleeve 50 and the biopsy can be obtained as described above (step C in FIG. 7).

Whereas all other elements are moveable parts, the fibre body 40 may virtually remain at a fixed position during the entire procedure. Since the fibre body 40 with the integrated optical fibres 44 is not moved, the design is compatible with fast (fully-automated) shooting mechanisms, where the workflow steps B and C are successively executed at high speed. Thus, the risk of damaging the optical fibres 44 by strong mechanical forces can be circumvented.

The length and position of the main shaft 10 may be chosen in such a way that the fibre body 40 is facing the proximal side of the notch 16 when exposed after the ejection (step B). This allows for a direct characterization of the tissue present in the notch 16, just before the biopsy is taken (step C). With this option, a confirmation measurement from the tissue in the notch can be performed in-situ, and an optimal correlation between the biopsy sample and the optical measurement can be ensured. This is particularly useful for biopsy devices with a manual or semi-automated shooting mechanism, where the workflow steps 2 and 3 can be executed with a user-defined time delay to allow for additional tissue measurements in the notch.

As a further feature, an opening for applying vacuum can be realized within the main shaft, the tube shaft and/or in the fibre body, and it may be used for sucking tissue into the notch 16 after the main shaft 10 has been ejected (step B) to ensure that the biopsy is of sufficient size. By way of this, the vacuum may also ensure that the tissue is brought in close contact with the optical fibres 44 facing the proximal side of the exposed notch 16, for the case that the tissue in the notch is characterized prior to obtaining the biopsy. It is noted that such an opening for applying vacuum may also be formed as a gap between the tube shaft 30 and the main shaft 10 or between the tube shaft 30 and the fibre body 40.

The incorporation of a small opening for applying vacuum can also allow for simultaneous biological/physiological analysis of the blood/tissue under consideration, thus obtaining a better biopsy quality. The vacuum can be used to suck in small amounts (microliter) of body fluid (for instance blood/serum, bile, or else) for instant biochemical analysis, which can be used to complement the optical tissue characterization.

For this, the vacuum is preferably realized by a small vacuum opening within or at the fibre body, so that the blood sampling can be performed within the described design at the tip (workflow step A in FIG. 7) and also in the notch (step B in FIG. 7).The absorbed blood/cells could be analyzed by appropriate detectors (such as chip-sized microfluidic devices and/or MEMS) connected to the distal end of the vacuum channel, thereby enabling instantaneous analysis.

For instance, MEMS-based pH sensors could allow for complementary classification of tumor (acidic) vs. normal (basic) tissue based on pH. Apart from pH sensors, also other specific sensors may be used that could characterize the tissue sample in consideration. This could serve as complimentary means to support the optical tissue sensing in difficult cases, and thereby improve the results of photonic biopsy procedures even further.

The optical fibres and the vacuum channel may be integrated into the shaft and/or fibre body in a way to ensure (1) a sufficiently large fibre distance for tissue characterization, and that (2) the opening has an appropriate size for sucking the tissue samples into the biopsy tube without hampering the stability of the shaft and/or fibre body.

It is noted that the 'bevel' might also have another shape or structure at the tip of the device, useful for introducing the device into a tissue. For example, the bevel might be a convex or concave surface, or the bevel might be a combination of several small surfaces, wherein these surfaces are connected to each other by steps or edges. It might also be possible that the cross section of the shaft is not completely cut by the bevel, such that an area remains which is blunt, i.e. is for example perpendicularly orientated relative to the longitudinal axis of the shaft. Such a 'blunt' end might include rounded edges or might also form a rounded leading edge. As another example, a sharp edge might be formed by two or more slanted surfaces being symmetrically or asymmetrically arranged to form the tip of the device.

Figure 8:
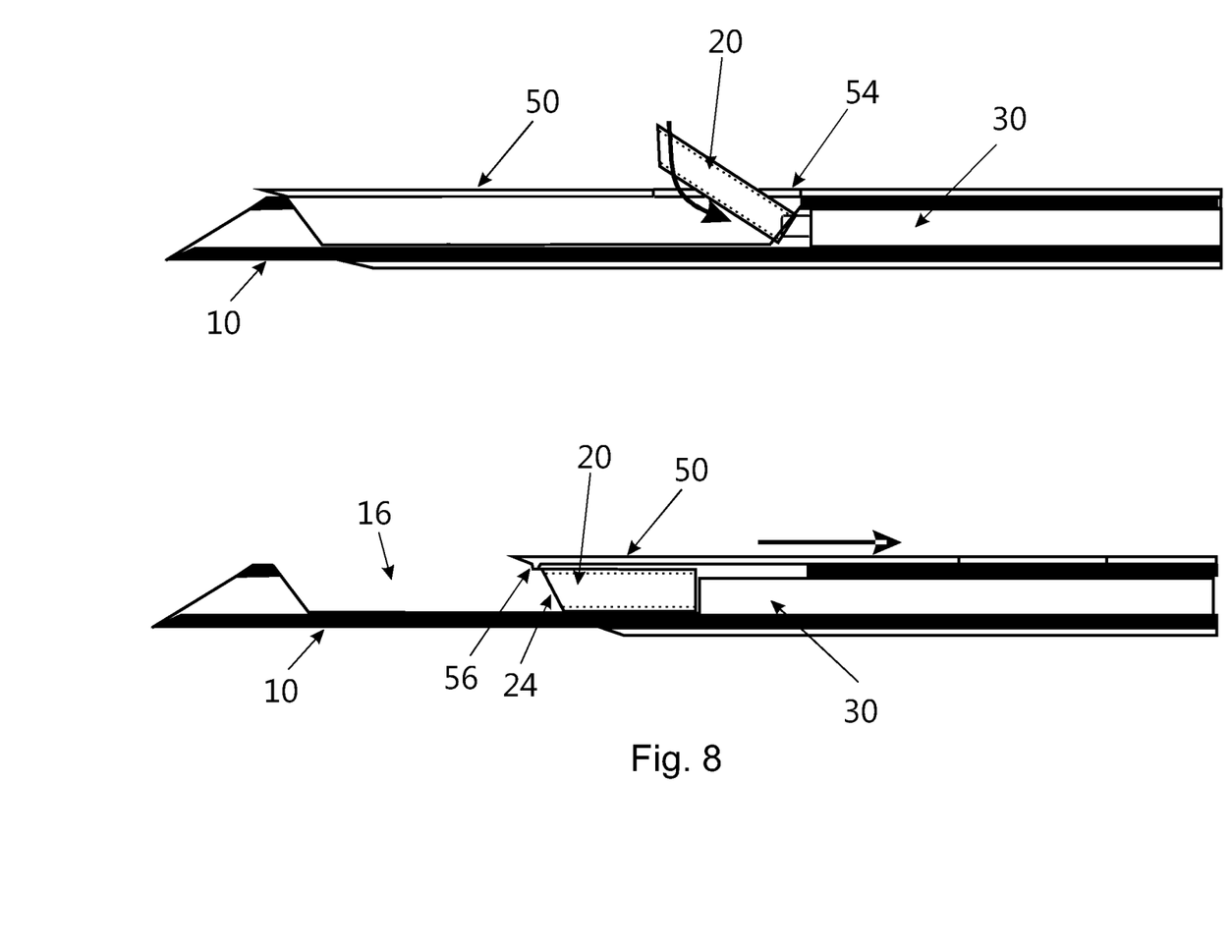
FIG. 8 illustrates steps of inserting a biopsy tube into a recess of a main shaft of a biopsy device, according to a third embodiment.

FIG. 8 shows another embodiment of a biopsy device having a main shaft 10, a biopsy tube 20, a tube shaft 30 and an outer sleeve 50, wherein the outer sleeve comprises a side opening 54 through which the biopsy tube 20 can be inserted into the main shaft 10 and in front of the tube shaft 30. This embodiment differs from the above described embodiments in that the outer sleeve 50 further comprises an inwardly protruding edge 56. The inwardly protruding edge 56 is configured to permit a movement of the biopsy tube 20 from proximal beyond that edge 56. In other words, the distal end 24 of the biopsy tube 20 may abut at the inwardly protruding edge 56. This embodiment provides the possibility of using a biopsy tube with a greater outer diameter. The biopsy tube may be arranged directly at an inner surface of the outer sleeve 50 and not inside a channel of the main shaft 10. Consequently, the wall of the hollow main shaft is partially removed so that the notch 16 and the side recess 18 together form a longer open portion for accommodating a larger biopsy tube and for allowing a movement of that biopsy tube within that longer open portion. Further, as can be seen in FIG. 8, the longitudinal center axis of the biopsy tube may be parallel but not congruent to the longitudinal center axis of the main shaft 10 and/or of the tube shaft 30.

Figure 9:
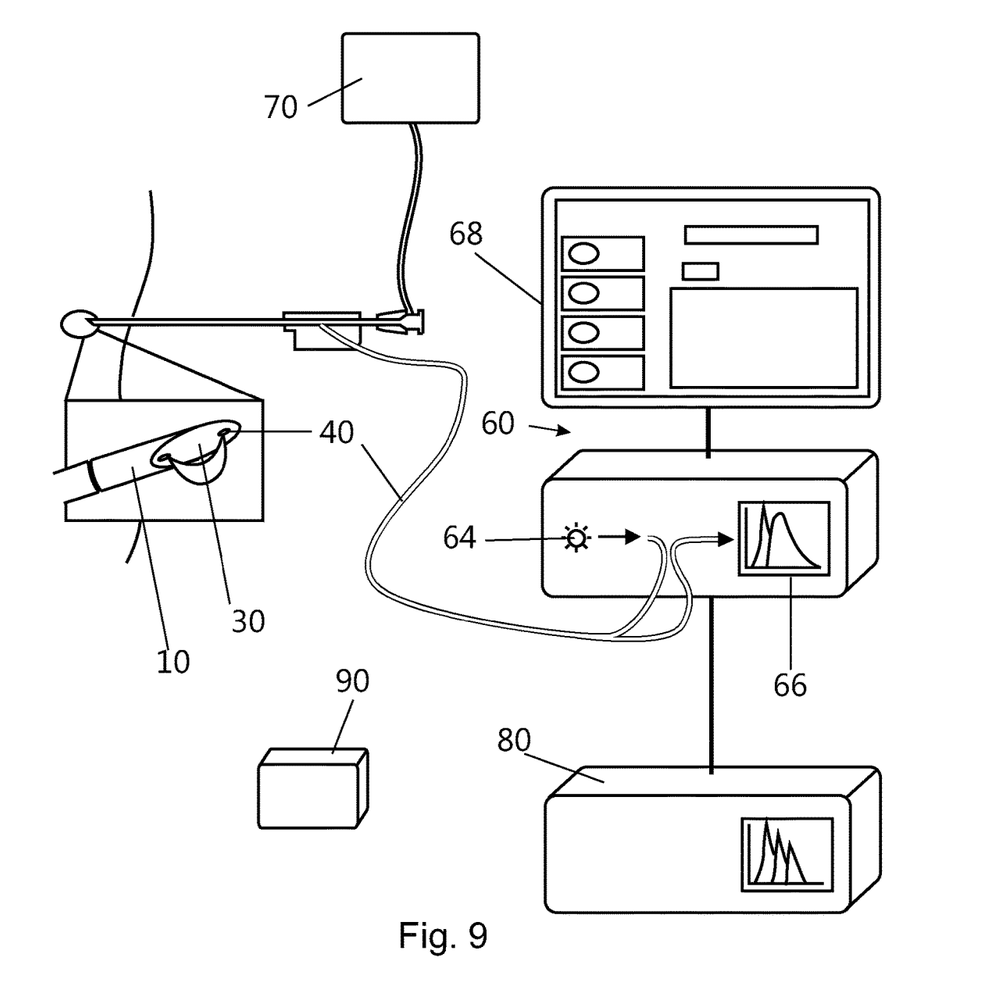
FIG. 9 shows a system including a biopsy device and a console.

As shown in FIG. 9, the fibres 44 of the interventional device may be connected to an optical console 60. The optical fibres can be understood as light guides or optical waveguides. In an embodiment, the console 60 comprises a light source 64 in the form of a halogen broadband light source with an embedded shutter, and an optical detector 66. The optical detector 66 can resolve light with a wavelength substantially in the visible and infrared regions of the wavelength spectrum, such as from 400 nm to 1700 nm. The combination of light source 64 and detector 66 allows for diffuse reflectance measurements. For a detailed discussion on diffuse reflectance measurements see R. Nachabe, B. H. W. Hendriks, A. E. Desjardins, M. van der Voort, M. B. van der Mark, and H. J. C. M. Sterenborg, "Estimation of lipid and water concentrations in scattering media with diffuse optical spectroscopy from 900 to 1600 nm", J. Biomed. Opt. 15, 037015 (2010).

Optionally it is also possible that the console is couple to an imaging modality capable of imaging the interior of the body, for instance when the biopsy is taken under image guidance. In this case it is also possible to store the image of the interior when the biopsy is taken to a container of the biopsy. In this case the in-vivo information of the optical biopsy needle, the information of the pathology of the biopsy as well as the location where the biopsy was taken may be brought together for advanced pathology.

On the other hand, also other optical methods can be envisioned like diffuse optical tomography by employing a plurality of optical fibres, differential path length spectroscopy, fluorescence and Raman spectroscopy to extract tissue properties.

Further shown in FIG. 9 are a suction device 70, a device 80 for obtaining ex-vivo pathology information, and a storage container 90. The suction device may be connected to a proximal end of the biopsy device, such that underpressure or a vacuum can be applied through the biopsy device to the distal end of the same, in particular to the notch at the distal end of the biopsy device.

The device 80 may be connected to the console 60 by means of a wire or wireless, for interchanging information like control commands or data representing pathological aspects of an inspected tissue sample. The device 80 may be a digital pathology systems consisting of an optical scanner and an image management system to enable digitizing, storage, retrieval, and processing of tissue staining images, reading the information stored in the storage box container, and integrating this information with the digitized staining data set, to be presented to the pathologist. In addition to this, the data set from the photonic biopsy device may be either presented next to the histopathology image or the two data sets may be fused in the image, characterized and recognizable by a certain coloring pattern of the image. For instance the oxygenation level measured in-vivo could be added as a red color, where deep red means low oxygenation and bright red would mean high oxygenation level. Additionally, molecular spatial distributions from FTIR or Raman could be added as a color coded mapping to the pathology slide of specific molecules.

The tissue sample, which may firstly be subjected to an in-vivo tissue inspection, i.e. an inspection within a living body, and which may secondly subjected to an ex-vivo tissue inspection by means of the device 80, may be situated in the container 90. Molecular diagnostics can also be performed on the tissue biopsy (e.g. sequencing or PCR), or part of the biopsy.

The storage container for the biopsy may further be such that the optical information obtained in-vivo and/or ex-vivo can be stored on it. This can be a barcode label which can be read at the pathology department by the digital pathology device. It can also be a microchip where the optical information can be stored electronically. Instead of storing the actual information it is also possible to store an "address" or "link" of where the information may be retrieved.

According to another embodiment, the container 80 may be placed in the console 60. The data can then be written on the container while the photonic biopsy device is attached to the console. The data can be written in the form of a barcode or can electronically be stored in the chip on the container.

A processor transforms the measured spectrum into physiological parameters that are indicative for the tissue state and a monitor 68 may be used to visualize the results.

A computer program executable on the processor may be provided on a suitable medium such as an optical storage medium or a solid-state medium supplied together with or as part of the processor, but may also be distributed in other forms, such as via the Internet or other wired or wireless telecommunication systems.

For fluorescence measurements the console must be capable of providing excitation light to at least one source fibre while detecting tissue-generated fluorescence through one or more detection fibres. The excitation light source may be a laser (e.g. a semiconductor laser), a light-emitting diode (LED) or a filtered light source, such as a filtered mercury lamp. In general, the wavelengths emitted by the excitation light source are shorter than the range of wavelengths of the fluorescence that is to be detected. It is preferable to filter out the excitation light using a detection filter in order to avoid possible overload of the detector by the excitation light. A wavelength-selective detector, e.g. a spectrometer, is required when multiple fluorescent entities are present that need to be distinguished from each other.

In case fluorescence measurements are to be combined with diffuse reflectance measurements, the excitation light for measuring fluorescence may be provided to the same source fibre as the light for diffuse reflectance. This may be accomplished by, e.g., using a fibre switch, or a beam splitter or dichroic beam combiner with focusing optics. Alternatively, separate fibres may be used for providing fluorescence excitation light and light for diffuse reflectance measurements.

The described devices can be used in minimally invasive needle interventions such as low-back pain interventions or taking biopsies in the field of cancer diagnosis or in case where tissue characterization around the needle is required.

In the following, exemplary needle devices will be described with respect to their outer diameter, their insertion length, and their preferred use.

A biopsy needle might have an outer diameter of 1.27 mm up to 2.108 mm, might be inserted into tissue with 100 mm to 150 mm of its length, and might be used in soft tissue core biopsies in the neck, the head, the breast, the prostate, and the liver.

A fine aspiration needle of soft tissue might have an outer diameter between 0.711 mm and 2.108 mm, might be inserted into soft tissue with 100 mm to 150 mm of its length, and might be used for aspiration of soft tissue.

A brain biopsy needle might have an outer diameter of 2.108 mm, might be inserted into tissue with 150 mm up to 250 mm of its length, and might be used for diagnostic brain biopsies.

Finally, the device may include a needle electrode having an outer diameter of 2.108 mm and smaller, the electrode might be inserted into tissue up to 250 mm of its length, and might be used for radio frequency ablation for instance of tumours.

According to an example, the diameter of the channel inside the main shaft may be 0.91 mm and the outer diameter of the tube shaft and the biopsy tube may be slightly less than that. The outer diameter of the main shaft may be 1.4 mm which may be combined with a loose fit inside an outer sleeve which may have an outer diameter of 1.65 mm. The notch may have a length of 17 mm.

According to another example, the dimensions of the tube shaft, the main shaft and the outer sleeve may be adapted to a biopsy tube with an outer diameter of 2 mm.

While the invention has been illustrated and described in detail in the drawings and foregoing description, such illustration and description are to be considered illustrative or exemplary and not restrictive; the invention is not limited to the disclosed embodiments. Other variations to the disclosed embodiments may be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

LIST OF REFERENCE SIGNS 10 main shaft
12 channel of main shaft
14 distal tip
16 notch
18 recess
20 biopsy tube
22 proximal end
23 alignment groove
24 distal end
26 longitudinal axis
28 channel of biopsy tube
30 tube shaft
31 alignment protrusion
32 first end
33 end portion
34 second end
36 longitudinal axis
38 channel of tube shaft
40 fibre body
42 optical fibre
44 end surface of fibre body
50 outer sleeve
52 cutting edge
54 lateral opening
56 inwardly protruding edge
60 console
64 light source
66 light detector
68 monitor
70 suction device
80 device for ex-vivo tissue inspection
90 storage container
100 shaft
200 notch
500 outer member

The invention claimed is:

1. A biopsy device to sample tissue, comprising
an outer sleeve,
a hollow main shaft, the hollow main shaft having a distal end portion, wherein a sideward facing notch is formed in the hollow main shaft in the distal end portion of the hollow main shaft, wherein the hollow main shaft is accommodated within the outer sleeve,
wherein the outer sleeve is movable relative to the hollow main shaft between a first position in which the notch is not covered by the outer sleeve, and a second position in which the notch is covered by the outer sleeve,
a tube shaft movably accommodated within the hollow main shaft, the tube shaft comprising a protrusion disposed at or adjacent to a distal end of the tube shaft, and
a biopsy tube for receiving tissue to be resected, the biopsy tube comprising a groove at a proximal end, the groove being configured to engage the protrusion disposed at or adjacent to a distal end of the tube shaft, wherein the biopsy tube is adapted to be inserted through the notch to releasably attach the proximal end of the biopsy tube to the distal end of the tube shaft, so that the biopsy tube is movable together with the tube shaft within the hollow main shaft between a proximal position in which the biopsy tube is not located in the notch, and a distal position in which the biopsy tube is located in the notch, wherein the tissue is resected and received within the biopsy tube when the outer sleeve is moved to the second position covering the notch and the biopsy tube is moved to the distal position such that the biopsy tube is located within the notch.

2. The biopsy device of claim 1, wherein the outer sleeve comprises an inwardly protruding edge for an abutment of the distal end of the biopsy tube so that the biopsy tube is movable together with the tube shaft and the outer sleeve.

3. The biopsy device of claim 1, wherein the tube shaft comprises a portion of the distal end with a smaller diameter.

4. The biopsy device of claim 3, wherein a suction channel is provided in the tube shaft.

5. The biopsy device of claim 1, further comprising at least one optical fibre for emitting and receiving of light, allowing in-vivo tissue inspection including at least one out of the group consisting of diffuse reflectance spectroscopy, fluorescence spectroscopy, diffuse optical tomography, differential path length spectroscopy, and Raman spectroscopy.

6. The biopsy device of claim 5, wherein the tube shaft is formed as a hollow tube shaft, the biopsy device further comprising an elongated fibre body with the at least one optical fibre arranged within the elongated fibre body, wherein the elongated fibre body is movably accommodated within the tube shaft, wherein the elongated fibre body is movable between a first position in which the elongated fibre body extends through the biopsy tube so that the distal end of the optical fibre is located at the distal end of the hollow main shaft, and a second position in which the distal end of the at least one optical fibre is located proximally to the notch.

7. A biopsy device of claim 6, wherein the biopsy tube is made of a transparent material.

8. The biopsy device of claim 6, wherein the biopsy tube is made of glass or a hard plastic material.

9. The biopsy device of claim 1, wherein the biopsy tube is coated with a silicone-coating.

10. The biopsy device of claim 1, wherein the biopsy tube has a length between 3 mm and 20 mm.

11. The biopsy device of claim 1, wherein the biopsy tube has an outer diameter of 2 mm, with an inner diameter between 1.5 mm and 1.6 mm.

12. The biopsy device of claim 1, wherein the biopsy tube comprises a sharp edge at the distal end of the biopsy tube.

13. The biopsy device of claim 1, wherein the groove and protrusion to identify a rotational orientation of the resected tissue during handling and analysis.

14. The biopsy device of claim 1, wherein the hollow main shaft comprises a surface slanted only on one side.

15. The biopsy device of claim 14, wherein the hollow main shaft has a circular cross-section, and the surface has an elliptical shape.

* * * * *